United States Patent [19]
Van

[11] Patent Number: 5,512,248
[45] Date of Patent: Apr. 30, 1996

[54] TWIN-PROBE BLOOD SAMPLE DILUTING DEVICE

[76] Inventor: Jack F. J. Van, 4 Fl., No. 151, Chen Ho Rd., San Ming Area, Kaohsiung, Taiwan

[21] Appl. No.: 345,696

[22] Filed: Nov. 21, 1994

Related U.S. Application Data

[63] Continuation-in-part of Ser. No. 155,841, Nov. 23, 1993, abandoned.

[51] Int. Cl.⁶ .................................................. G01N 1/14
[52] U.S. Cl. ...................... 422/100; 422/102; 436/180; 128/749; 128/760; 73/864.12
[58] Field of Search ................................. 422/100, 102; 436/180; 128/749, 760; 73/864.11, 864.12

[56] References Cited

U.S. PATENT DOCUMENTS

| | | | |
|---|---|---|---|
| 3,610,226 | 10/1971 | Albisser | 128/760 |
| 4,108,608 | 8/1978 | Maher, Jr. et al. | 73/864.12 |
| 4,399,711 | 8/1983 | Klein | 422/100 |
| 4,528,158 | 7/1985 | Gilles et al. | 436/180 |
| 4,817,631 | 4/1989 | Schnipp-Pesch et al. | 128/749 |
| 4,877,585 | 10/1989 | Perlman | 436/180 |

FOREIGN PATENT DOCUMENTS

| | | | |
|---|---|---|---|
| 0115190 | 9/1979 | Japan | 422/100 |
| 0639598 | 12/1978 | U.S.S.R. | 73/864.11 |

*Primary Examiner*—Jill Warden
*Assistant Examiner*—Harold Y. Pyon

[57] ABSTRACT

A blood diluting device that can be used in an automatic hematology cell counter, including an outer tube, and an inner tube suspended within the outer tube. A blood sample to be analyzed is aspirated into the outer tube and then the inner tube, and then air is induced into the outer tube to expel the blood sample outside the inner tube. Thereafter, air is induced into the inner tube to isolate the blood sample inside the inner tube to keep the two blood samples from mixing, so that two diluted blood samples of different dilution ratios can be obtained one after the other.

1 Claim, 4 Drawing Sheets

TWIN-PROBE BLOOD SAMPLE DILUTING DEVICE

ROSS REFERENCE TO RELATED APPLICATION

This application is a continuation-in-part application of U.S. Ser. No. 08/155,841, filed Nov. 23, 1993 now abandoned.

BACKGROUND OF THE INVENTION

The present invention is directed to a unique method and device for blood sample dilution, which can be used in an automatic hematology cell counter.

Before starting an analysis, a hematology cell counter must dilute the whole blood sample into two diluted samples, one of low dilution ratio for WBC (while blood cell)/HGB(hemoglobin) counting, one of high dilution ratio for RBC (red blood cell)/PLT (platelete) counting. From commonly used dilution methods, we may summarize two types of dilution methods, the Twice-Sampling method and the Single-Sampling method. Each method has its own advantages and drawbacks, describing as follows:

A. The Twice-Sampling method:

This method uses twice diluting to obtain high dilution ratio sample. The whole blood is aspirated through a sample probe by a sample syringe. After wiping off blood remaining on the outside the probe, the sampled blood inside the probe is dispensed by an isotonic diluent syringe to a bath. This diluted sample in the bath is the first low dilution ratio sample for WBC/HGB counting. Again, the probe aspirates the first diluted sample then sends it to the other bath. This second diluted sample is the high dilution ratio sample for RBC/PLT counting. Advantage: Low sample volume is needed, typically 20–40 μl. Drawbacks: (a) Because of its complicated procedure, it has low efficiency and low throughput. (b) A cleaning or washing procedure must be carried out to clean the outside wall of the probe after sampling.(c) A premixing cup or sample bath is opened up to a large extent. Therefore, dust particles can clog the counting orifice.

B. The Single-Sampling method

The whole blood sample is directly dispensed into two sample volumes for two dilution ratios. Commonly, a blood sampling valve (B.S.V.) is used. A B.S.V. is made of ceramics, comprised of three perforated circular plates connected one above another. As the blood sample is delivered from the sample probe through the valve, the intermediate plate is turned to collect two separated sample volumes for two different dilution ratios, then the diluent is sent to respective holes on the valve to flush diluted samples into two counting baths respectively. The intermediate plate is then turned back to its blood sampling home position. And the blood sample passing path is cleaned by sending the diluent through the passage to the waste. Advantage: Only one sampling is used achieving higher efficiency and higher throughput. Drawbacks: (a) Because it has a long path for its blood sample sucking stroke, typically around 100 μl, a large sample volume is needed. (b) Liquid leakage may occur during the rotary motion of the intermediate cylindrical section. Accordingly, the B.S.V. must be regularly maintained.

SUMMARY OF THE INVENTION

The present invention has been accomplished to provide a twin-probe blood diluting device which has high throughput, low sample volume, and eliminates the aforesaid drawbacks. According to the preferred embodiment of the present invention, the twin-probe blood diluting device is generally comprised of an outer tube, and an inner tube suspended within the outer tube. The blood sample is aspirated into the outer tube first and then into the inner tube to collect two sample volumes in these two tubes. The blood residue is wiped off the exterior of the outer tube outside wall. Air is induced into the outer tube to expel the sampled blood up off the inner tube, and then a little air is induced into the inner tube to isolate the sample blood inside the inner tube to prevent sample mixing while the diluent in the outer tube is flushed, and therefore two dilution ratio samples can be obtained by dispensing the diluent through the outer tube and then through the inner tube one after the other.

Pertaining to a series of tests, the present invention achieves various advantages as follows:

i) It is a single-sampling method. The twin-probe directly picks up two sample volumes for two dilution ratios. The method provides high efficiency and throughput.

ii) It is like a two-sampling method. Only a very low sample volume is needed for a test. The method is especially suited for those medical departments that can only take a small amount or volume of blood for samples.

iii) There is no liquid leakage, no regular maintenance is needed only the need to wipe the probe once. No other cleaning procedures are needed.

iv) Through a probe adapter, the diluted sample is directly dispensed into the counting baths. Thus, no dust particles can contaminate the sample.

v) The same blood sample is analyzed repeatedly. It gives a high precision.

vi) Low, normal, and high blood samples are tested. This provides a good correlation.

vii) No significant difference is shown in the examination results, if a 1.6 μl RBC/PLT blood sample is aspirated into the inner tube 10 minutes after the aspiration of 24 μl WBC/HGB blood sample into the outer tube. This means that the diluent contained in the inner tube does not dilute the surrounding blood sample in 10 minutes. In actual practice, there is only 1–2 seconds of time difference for blood sampling between the inner tube and the outer tube.

viii) No significant difference is shown on the examination results if a waiting period of 10 minutes before expelling the air to isolate the samples in the tubes is used. This means the blood sample contained in the inner tube does not sink or drip into the outer tube in 10 minutes. In actual practice, the time interval between the sampling and the isolating does not exceed 15 seconds.

BRIEF DESCRIPTION OF THE DRAWINGS

The present invention will now be described by way of example with reference to the annexed drawings in which.

DETAILED DESCRIPTION OF THE PREFERRED EMBODIMENTS

Figure 2:
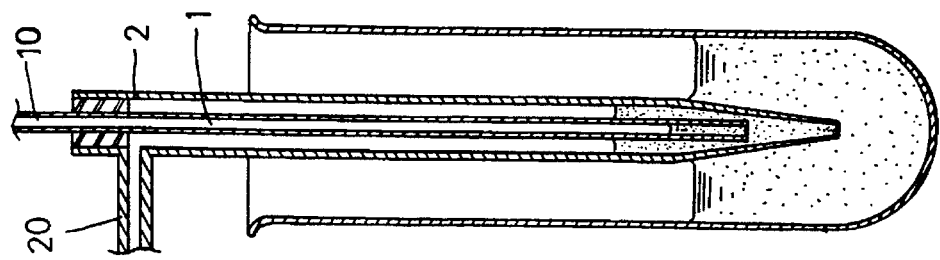
FIG. 2 is a sectional plan view of the twin-probe blood diluting device of FIG. 1 operated to suck in a blood sample.
Figure 1:
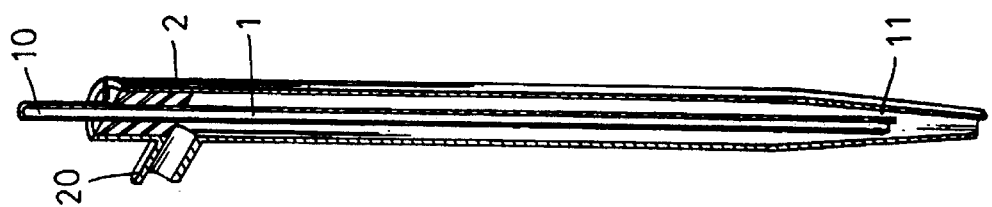
FIG. 1 is a cutaway view of the twin-probe of the blood diluting device according to the preferred embodiment of the present invention.
Figure 3:
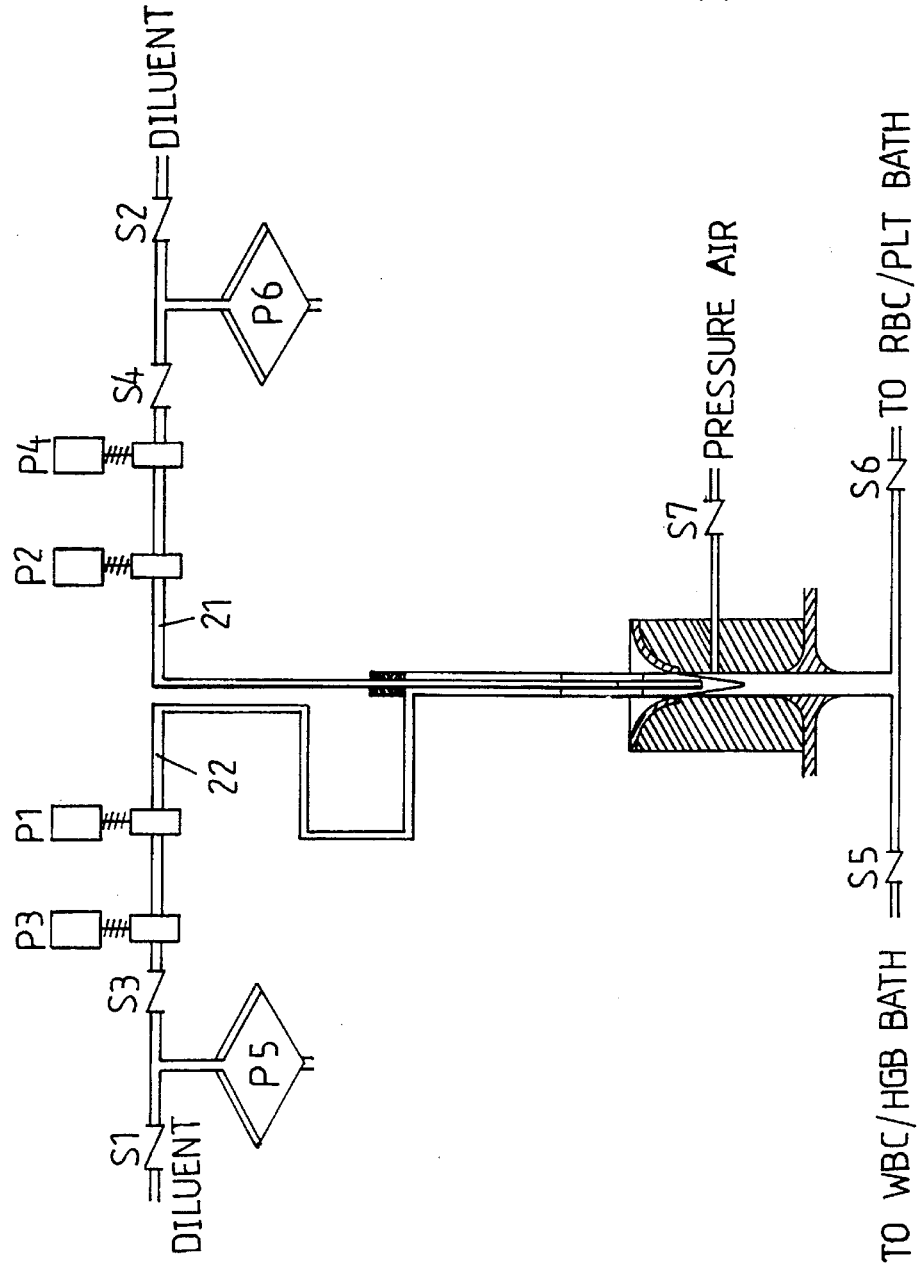
FIG. 3 shows the arrangement of the present invention when applied to an automatic hematology cell counter.

Referring to FIGS. 1, 2, 3, a blood diluting device in accordance with the preferred embodiment of the present invention is generally comprised of an inner tube, and an outer tube 2. The inner tube I is made of a stainless steel tube or tube of other appropriate material and can have caliber 1/32 inch. The tube is coaxially disposed within the outer tube 2, having an upper part retained within the top end of the outer tube 2. The top end 10 of the inner tube I extends out of the blocked or stopped top end of the outer tube 2 for connection to, for example, a 1.6 μl (microliter) electromagnetic micropipette P2 and a 0.6 μl electromagnetic micropipette P4 through a hard tube 21. The bottom end 11 of the inner tube I is suspended within the outer tube 2 and can be spaced about 4 mm above the bottom end of the outer tube 2. The outer tube 2 is made of a stainless steel tube or tube of other suitable material of, for example, caliber 3 mm. The bottom end of the outer tube 2 has a gradually reducing diameter towards its bottom tip. The diameter or caliber of the tip of the bottom end of the outer tube 2 can be about 1 mm. The outer tube 2 has an upper port 20 near the blocked top end thereof for connection to two 24 μl electromagnetic micropipettes P1, P3 through a hard tube 22.

Figure 8:
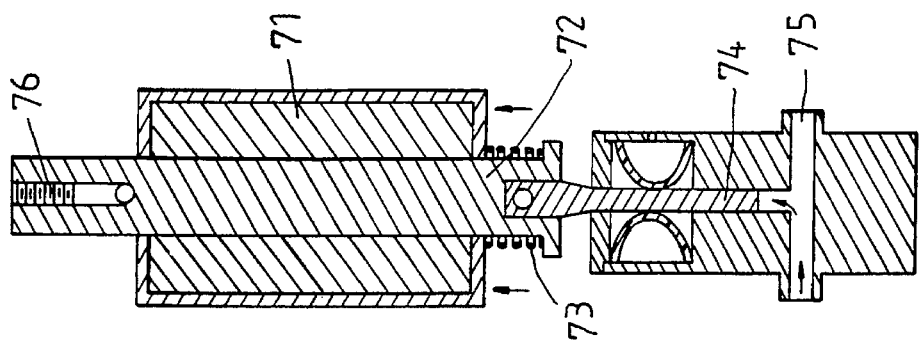
FIGS. 7 and 8 are cross-sectional views of an electromagnetic micropipette that can be used in the present invention.
Figure 7:
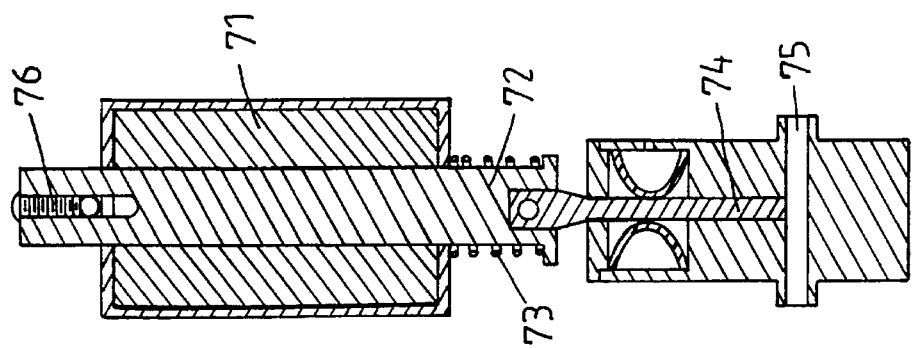

Electromagnetic micropipettes that can be used in the present invention for the electromagnetic pipettes P1, P2, P3 and P4 include those shown in FIGS. 7 and 8. These electromagnetic micropipettes comprise a magnetic coil device 71, a metal core 72 inserted through the magnetic coil 71 in the axial direction, a spring 73 mounted around the core 72 and arranged between the magnetic coil device 71 and the flanged front end of the core 72 and biasing the core 72 downward, a plastic axial rod 74 having a diameter of, for example, 3 mm and having one end coupled to the core 72 and an opposite end inserted into the micropipette body and coupled to the air hole 75 on the micropipette body, and an adjusting screw 76 fastened to the rear end of the core 72 to control the longitudinal moving range of the core 72 in the magnetic coil body 71. The magnetic coil 71 device can comprise a helically wound coil or wire having the ends thereof electrically connected to an electrical power source through a switch. When the electromagnetic micropipette is activated by passing an electric current though the magnetic coil device 71, the magnetic coil device becomes highly magnetized and the resulting magnetic field pulls the core 72 upward. FIG. 7 shows the electromagnetic micropipette in a resting state, and FIG. 8 shows the electromagnetic micropipette in an activated state. When the adjusting screw 76 is turned inward, the stroke of the core 72 is shorten and, therefore, less suction force is produced so that a smaller amount of blood sample is sucked in by the micropipette. On the other hand, when the adjusting screw is turned outward, the stroke of the core 72 is extended, and therefore the suction force of the electromagnetic micropipette is increased and a higher amount of blood is sucked in. By this adjustment, the inner and outer tubes can be controlled in the present invention to dilute blood samples at different rates.

Figure 4:
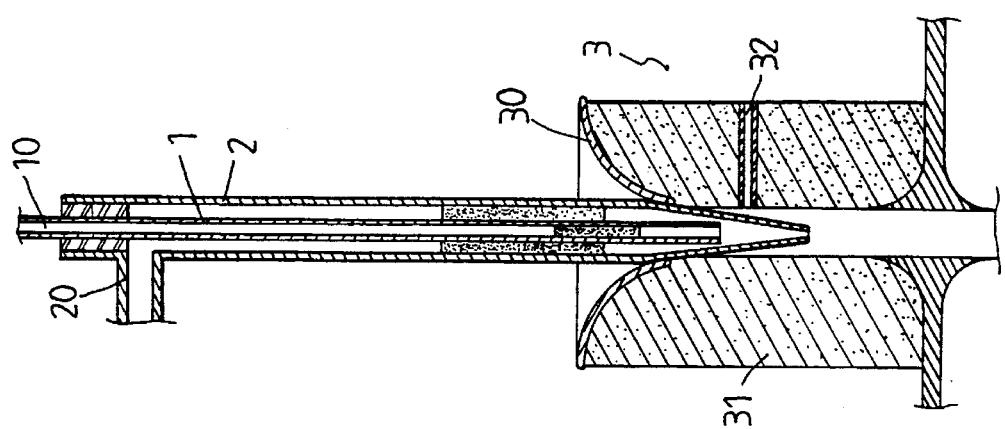
FIG. 4 shows the probe adapter and the twin-probe blood diluting device operated to expel air to isolate the blood sample in the inner tube.

Referring to FIG. 4, there is shown a probe adapter 3 for guiding the diluted blood samples from the twin-probe to two different counting baths. The adapter body 31 of the adapter 3 is made of rubber or other appropriate material that can be squeezed to seal the probe, having a horn-shaped mounting guide 30 on the top thereof made of a hard material that gradually increases in size toward the outside for guiding the twin-probe without causing direct contact of the inside wall of the adapter body 31 with sampled blood being sent therethrough. An air hole 32 is provided for drawing off positive pressure. The bottom of the adapter 3 is terminated by a three-way connector which will be explained further below. As the sample probe is settled down inside the adapter 3, the air hole 32 is disposed at a higher elevation than the tip of the sample probe. When the diluent is drawn off from the sample probe, air is drawn away from the adapter 3 through the air hole 32, and therefore no liquid drops will reside outside the probe. Also, the air will be in the three-way connector for isolating the diluted sample flowing there-through.

Figure 5:
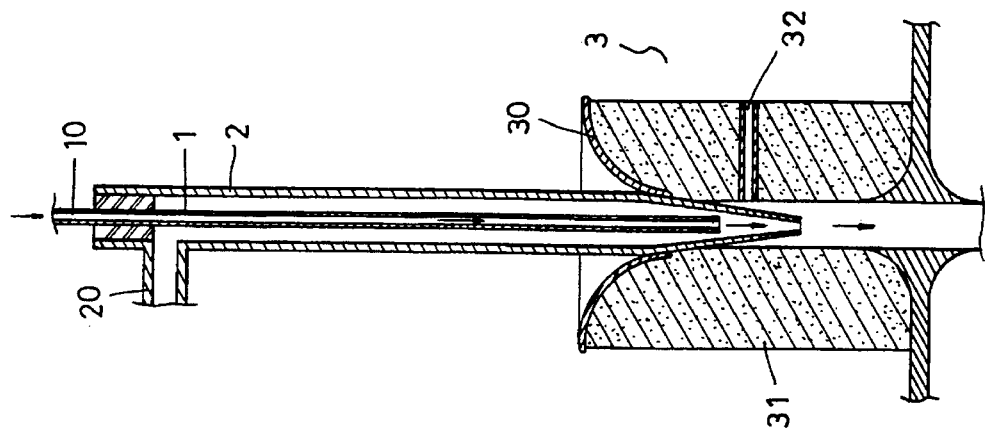
FIG. 5 shows the twin-probe blood diluting device operated to dispense the blood sample in the outer tube to WBC/HGB bath.
Figure 6:
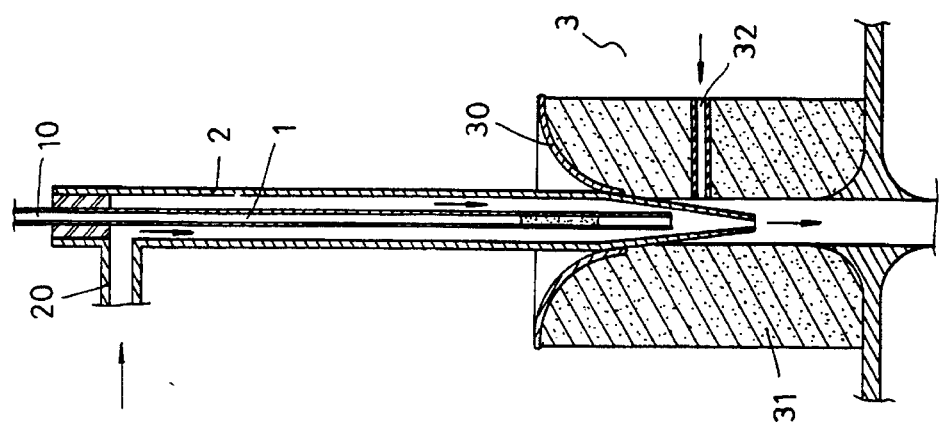
FIG. 6 shows the twin-probe blood diluting device operated to dispense the blood sample in the inner tube to RBC/PLT bath.

Referring to FIGS. 5 and 6, and FIGS. 3 and 4 again, before starting an operation, the twin-probe is filled with diluent. After the whole blood sample was prepared, the diluting operation is then executed as follows:

i) The first electromagnetic micropipette P1 is turned on to suck 24 μl of the blood into the outer tube 2 permitting the outside wall of the inner tube I to be covered with the sampled blood, then the second electromagnetic micropipette P2 is turned on to suck 1.6 μl of the blood into the inner tube 1.

(ii) The whole blood sample is moved away when the machine buzzes, then any blood residue is wiped off the outer tube 2 while the 1.6 μl of the sampled blood is retained in the inner tube 1.

(iii) The probe is attached to the adapter 3. When the probe is settled in the adapter, the third electromagnetic micropipette P3 is turned on to suck in 24 μl of air for expelling the blood surrounding the inner tube 1 and for moving the blood upwards out of the outer tube 2, and then the fourth electromagnetic micropipette P4 is turned on to suck 0.6 μl of air into the inner tube to block up the sampled blood being retained in the inner tube. Therefore, the blood sample in the inner tube will not be carried away as the outer tube 2 is dispensed with the diluent.

(iv) The first electromagnetic valve S1 and the second electromagnetic valve S2 are turned on, so that the first diaphragm pump P5 and the second diaphragm pump P6 respectively suck in 5 cc of the diluent.

(v) The first electromagnetic valve S 1 is turned off, and the third electromagnetic valve S3 and the sixth (normal open) electromagnetic valve S6 are turned on, therefore the first diaphragm pump P5 discharges 5 cc diluent and 1 cc of HGB Lysing reagent is added to the WBC/HGB counting bath. Then, the first electromagnetic micropipette P1 and the third electromagnetic micropipette P3 are turned off, and the seventh electromagnetic valve S7 is turned on for a certain length of time permitting the diluent to be completely expelled to the counting bath. Therefore, a diluted sample of a low dilution ratio of, for example, 1:251 is obtained in the WBC/HGB counting bath.

(vi) At this stage, the outside wall of the inner tube I is cleaned by the diluent. The three-way connector is full of the air for isolating the sampled blood flowing through. Then, the second electromagnetic valve S2 is turned off, the fourth electromagnetic valve S4 and the fifth (normal open) electromagnetic valve S5 are turned on, and the sixth electromagnetic valve S6 is turned off, and the second diaphragm pump P6 expels 5cc of the diluent to the RBC/PLT counting bath. At the same time, the first electromagnetic valve S 1 is turned on and the third electromagnetic valve S3 is turned off, and therefore the first diaphragm pump P5 sucks in 5cc of the diluent again, the first and fourth electromagnetic valves S1; S4 are turned off, the second and fourth electromagnetic micropipettes P2; P4 are turned off, and the third electromagnetic valve S3 is turned on, and 5 cc of the diluent is expelled to the RBC/PLT counting bath; the seventh electromagnetic valve S7 works as above explained, the third and fifth electromagnetic valves S3; S5 are turned off. Therefore, a diluted sample of high dilution ratio of, for example, 1:6251 is obtained in the RBC/PLT counting bath.

(vii) The inner and outer tubes 1,2 of the twin-probe are filled up with the diluent after the diluting operation is completed, and no residual liquid is retained around the tip of the probe. The probe is settled in the adapter 3, and all the electromagnetic valves are off during the standby mode.

As indicated above, the twin-probe sampling and diluting process of the present invention is efficient and simple, and less volume of the blood sample is needed for testing. While only one preferred embodiment of the present invention has been shown and described, it will be understood that various modifications and changes could be made without departing from the spirit and scope of the invention.

I claim:

1. A blood diluting device comprising:

a tube assembly including an outer tube having a cone-shaped bottom end of a gradually reducing diameter, a top end sealed with a plug, and an intake port near the top end thereof; and an inner tube concentrically suspended within said outer tube, having a top end extending out of a center hole on the plug of said outer tube, said intake port of said outer tube connected by a first tube respectively to a parallel set of first and third electromagnetic micropipettes, a third electromagnetic valve, a first pump, a first electromagnetic valve and supply of diluent;

said top end of said inner tube connected by a second tube respectively to a parallel set of second and fourth electromagnetic micropipettes, a fourth electromagnetic valve, a second pump, a second electromagnetic valve and supply of diluent; and an adapter having a hollow center, an air hole and a bottom terminated by a three-way connector, said air hole connected to a seventh electromagnetic valve, said three-way connector having a first connection to said hollow center of said adapter, a second connection to a first counting bath through a normally opened fifth electromagnetic valve and a third connection to a second counting bath through a normally opened sixth electromagnetic valve, wherein said blood diluting device operates as follows:

(1) said first and second micropipettes are activated to suck a blood sample to be analyzed respectively into the outer tube and then the inner tube, (2) said tube assembly is placed in said adapter with said outer tube received in said hollow center, so that said adapter and said outer tube are sealed together and said air hole is arranged above said bottom end of said outer tube, (3) said third micropipette is activated to drawn air into the outer tube, and then said fourth micropipette is activated to draw air into the inner tube, so that the blood sample of said inner tube is isolated from the blood sample in said outer tube, (4) said first and second valves are activated to respectively suck diluent into said first and second tubes by action of said first and second pumps, (5) said first valve is deactivated and said third and sixth valves are activated, so that said first pump discharges said sample from said outer tube and then said diluent toward said first counting bath, (6) said first and third micropipettes are deactivated and said seventh valve is activated permitting said diluent to be completely expelled to said first counting bath, (7) said second and sixth electromagnetic valves are deactivated and the fourth and fifth valves are activated, so that the second pump discharges said sample contained in said inner tube and then said diluent toward said second counting bath and, at the same time, said first valve is activated and said third valve is deactivated, so that said first pump sucks additional diluent into said first tube, and (8) said first and fourth valves are deactivated, said second and fourth micropipettes are deactivated, and said third valve is activated causing said additional diluent to discharge into said second counting bath, resulting in the blood sample in said second counting bath having a greater dilution ratio than that of the blood sample in said first counting bath.

\* \* \* \* \*